(12) United States Patent
Bucataru

(10) Patent No.: US 11,944,771 B1
(45) Date of Patent: Apr. 2, 2024

(54) PERSONAL MEDICAL DEVICE FOR ADMINISTERING TREATMENT VIA MUCOUS MEMBRANE

(71) Applicant: Andrada Bucataru, Calgary (CA)

(72) Inventor: Andrada Bucataru, Calgary (CA)

(*) Notice: Subject to any disclaimer, the term of this patent is extended or adjusted under 35 U.S.C. 154(b) by 0 days.

(21) Appl. No.: 17/690,755

(22) Filed: Mar. 9, 2022

Related U.S. Application Data

(63) Continuation of application No. 17/226,043, filed on Apr. 8, 2021, now Pat. No. 11,684,760.

(60) Provisional application No. 63/083,874, filed on Mar. 29, 2021.

(51) Int. Cl.
| | |
|---|---|
| *A61M 31/00* | (2006.01) |
| *A61L 2/00* | (2006.01) |
| *A61L 2/26* | (2006.01) |
| *G06Q 10/0832* | (2023.01) |
| *G16H 10/40* | (2018.01) |
| *G16H 20/10* | (2018.01) |
| *G16H 40/63* | (2018.01) |

(Continued)

(52) U.S. Cl.
CPC ........... *A61M 31/00* (2013.01); *A61L 2/0047* (2013.01); *A61L 2/26* (2013.01); *G06Q 10/0832* (2013.01); *G16H 10/40* (2018.01); *G16H 20/10* (2018.01); *G16H 40/63* (2018.01); *A61J 1/05* (2013.01); *A61L 2202/11* (2013.01); *A61M 2209/06* (2013.01); *H02J 7/35* (2013.01)

(58) Field of Classification Search
None
See application file for complete search history.

(56) References Cited

U.S. PATENT DOCUMENTS

| | | | | |
|---|---|---|---|---|
| 4,440,161 A | * | 4/1984 | Wadhwa | ........... A61M 16/0472 128/207.29 |
| 2011/0152838 A1 | * | 6/2011 | Xia | ........................ A61M 11/06 604/514 |

(Continued)

FOREIGN PATENT DOCUMENTS

| | | | | | |
|---|---|---|---|---|---|
| CN | | 114099924 A | * | 3/2022 | |
| WO | WO-2021069972 A1 | * | 4/2021 | .......... A61M 11/007 |

OTHER PUBLICATIONS

Translation of CN-114099924-A (Year: 2022).*

(Continued)

*Primary Examiner* — Manuel A Mendez

(57) ABSTRACT

The invention claims a new type of handheld medical device is meant to help the medical community by enabling them to treat patients remotely. This solves the problem of patient suffering or death due to lack of access to a medical professional or long wait times by enabling a patient-centred response to diseases, such as COVID-19. The device is hand-held, with incorporated germicidal UVC lights, an internal application tip and the delivery mechanism focuses on the mucous membrane. The top chamber connects to a removable container which can be used with the prescribed treatment/therapy, vaccine, or viral testing fluid/reagent, as needed. The versatility, non-invasive nature and germicidal properties constitute distinct improvements over other similar medical devices. This device also promotes the development of non-invasive inoculation and drug delivery systems via the mucous membrane.

17 Claims, 2 Drawing Sheets

Figure 1:
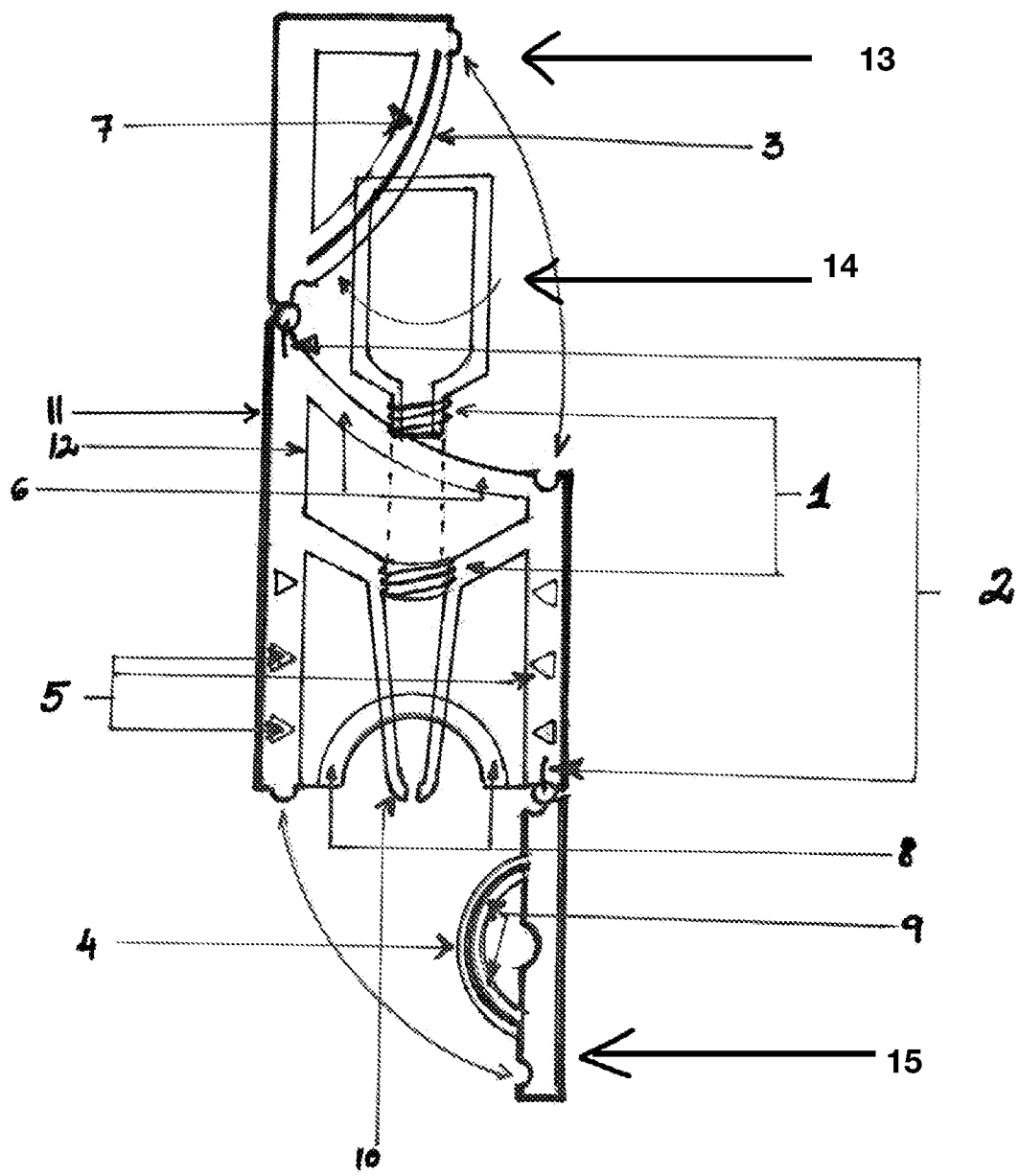

(51) Int. Cl.
    *A61J 1/05*           (2006.01)
    *H02J 7/35*          (2006.01)

(56)                   References Cited

U.S. PATENT DOCUMENTS

2020/0029714 A1*   1/2020   Nguyen  ................. C02F 1/325
2022/0347447 A1*  11/2022  Bucataru  .............. A61L 2/0047

OTHER PUBLICATIONS

Lemoine et al., Technological Approaches for Improving Vaccination Compliance and Coverage. (Year: 2020).*
Brito et al.; Designing and building the next generation of improved vaccine adjuvants. J Control Release. (Year: 2014).*
Emails 1 to 10 [Oct. 31, 2022 to Nov. 11, 2022]; Internet Communications made of record per MPEP 502.03. (Year: 2022).*
Emails 11-20 [Nov. 11, 2022 to Nov. 23, 2022]; Internet Communications made of record per MPEP 502.03. (Year: 2022).*
Emails 21-30 [Nov. 23, 2022 to Apr. 4, 2023; Internet Communications made of record per MPEP 502.03. (Year: 2023).*
Emails 31-40 [Apr. 4, 2023 to Apr. 13, 2023]; Internet Communications made of record per MPEP 502.03. (Year: 2023).*
Emails 41-50 [Apr. 18, 2023 to Apr. 26, 2023]; Internet Communications made of record per MPEP 502.03. (Year: 2023) (Year: 2023).*
Emails 51-60 [Jun. 11, 2023 to Jul. 6, 2023]; Internet Communications made of record per MPEP 502.03. (Year: 2023) (Year: 2023).*
Emails 61-80 [Jul. 8, 2023 to Nov. 1, 2023]; Internet Communications made of record per MPEP 502.03. (Year: 2023) (Year: 2023).*

* cited by examiner

PERSONAL MEDICAL DEVICE FOR ADMINISTERING TREATMENT VIA MUCOUS MEMBRANE

CROSS-REFERENCE TO RELATED APPLICATIONS

This application claims priority to U.S. Provisional Application Ser. No. 63/083,874, filed on Mar. 29, 2021, and titled 'Personal Medical device for administering treatment via mucous membrane', which is hereby incorporated by reference in its entirety.

STATEMENT REGARDING FEDERALLY SPONSORED RESEARCH OR DEVELOPMENT

Not applicable

SEQUENCE LISTING

Not applicable

BACKGROUND OF THE INVENTION

Traditional methods used to combat the spread of infection rely heavily on the use of hospitals. The current COVID-19 viral pandemic has illustrated clearly the danger of overwhelming the healthcare system and the direct toll it takes on both medical professionals and patients. In terms of preventing infection, the boosting of the immune system and the antibody response remains essential, in addition to antiviral drugs. A variety of treatments have been developed, with more yet to come.

For the purposes of this application the term "treatments" may refer to any approved treatment plan including drug therapies, convalescent plasma, vaccines, immunity-based booster shots and antigen/antibody testing. Where it was deemed relevant the distinction between "treatments" and "testing" was specified. Although testing is a crucial part of treating the patient, it presents a different process than dispensing a vaccine or antiviral drug.

However, we have seen the challenges of administering treatments. Bottlenecks in supplies and healthcare professionals present obstacles in North America and across the world. Injections remain the primary mode of administering treatment. Apart from the shortages encountered, injections also break the skin barrier resulting in the most common side effect, pain at the site of the injection. Additionally, they can pose an extra risk of spreading a secondary infection in communities known to be at a high risk of other infections; such as HIV. This can also be the case in regards to hospital acquired infections. Thus, this is a serious short fall for this type of treatment delivery system.

Another challenge is the mass manufacturing and safe disposal of syringes, and the clear need for injections to be administered by trained medical professionals. It is quite clear that this creates bottlenecks for receiving the treatment due to both supply and personnel shortages. This is also a concern for vaccines which really on cold chain, due to the lack of cold chain equipment in most hospitals around the world, and lack of funding to purchase such equipment in developing nations. Moreover, having to administer the vaccine/treatment in person, also puts medical personnel and first responders at the risk due to constant exposure to infected patients.

Vaccinations and drug delivery via mouth or nasal spray already exist; and the delivery of antibodies, particularly monoclonal antibodies, via aerosol particles has been well established for many years, and known to be highly effective. Therefore the ability to use less material than during an injection in order to induce the desired immune response is well documented in the art, and new systems of vaccine delivery are being considered as well. However, in the case of highly respiratory contagious viruses there is a very real risk of spreading infection via aerosols, thus putting healthcare professionals and the surrounding public at risk. Despite these concerns though, is already well established that the mucous membrane is the primary site for absorbing antigen and it can also be used to deliver the much smaller antibodies (Immunoglobulins), vaccines or prescribed drugs as well. There is simply no delivery system yet to take advantage of these characteristics outside a hospital setting for highly contagious viruses.

There is another barrier to vaccine development which is the time it takes to identify new viruses and to modify the virus or viral particles so that they may be used in vaccines. Typically this process takes months at least. In some cases vaccine development uses another virus as a delivery system. While this method avoids the need for cold chain it presents its own risks and relies on constant handling of viruses in lab settings. As we have seen it is quite possible for viruses to jump from animals to humans thus this presents a clear present and future danger. Therefore, this is another barrier to quick pandemic response and being able to combat new viruses.

Other therapies such as convalescent plasma, and Immunoglobulins have also been proven to have positive effects, provided that they can be administered as soon as possible after exposure. They do not require extensive research, due to past successful use, they simply require collection of the material, and distribution. Since these methods rely on using recovered patients naturally derived antibodies to fight infection in others, it is important to be able to deliver such treatments safely and as soon as possible. Dosage/concentration of antibodies and timing are the main limiting factors. However, this is simply not possible on a wide scale at the moment since such treatments require hospitalization.

In addition, while there are currently a variety of UVC germicidal products, it has been extremely difficult to translate these properties into useful products to combat highly infectious viruses. One hurdle is the need to not expose patients to damaging UVC light, thus limiting its usefulness. Therefore, it's current uses are based primarily in surfaces, air and water sanitization, and some surgical applications (where the primary focus is bacteria neutralization to prevent infection). While this gives us a good starting point it, there is still a clear need to improve upon the technology.

In conclusion, this personal medical device aims to address the highlighted problems: improve efficacy for the delivery of a variety of treatments, reduce the amount of treatment needed per application, insure sanitary conditions regardless of access to a hospital, decentralize treatment delivery for patients in order to prevent hospitalizations and reduce the severity of disease and the death toll. The approach focuses on decentralizing the delivery of treatments, enabling rapid shipping and safe use of the treatment products and creating the ability to use the treatment doses as effectively as possible in order to speed up the pandemic response.

Case Studies:

The most common pandemic scenario we have seen is travellers spreading the virus unknowingly. Due to the highly contagious nature of the virus hospital systems became overwhelmed quickly, and the death toll kept rising.

This led to the lockdowns and suspending of travel and tourism causing hardship, economic damage and an increase in mental health decline, due to the imposed isolation. This situation is made more challenging by the inability to use testing quickly to know for sure who is infected, or not. In addition, some viruses, such as COVID-19, have the ability to incubate for a long time before symptoms become evident, thus leading to significant transmission within the community.

In cases where infections can break out among isolated military members while abroad, as we witnessed during the beginning of the pandemic, it is virtually impossible to contain while members are all isolated in close proximity to each other. While it has not been expressly addressed, the risk of biological weapons has been mentioned in the news. Thus, there is a clear need to create immunity for at-risk persons immediately, while in isolation and lacking hospital equipment. The alternative would be to allow the infection to run its course and accept the death toll. That is clearly unacceptable and a scenario which demands a solution.

The isolation scenario also applies to seniors in nursing homes, or tourists on cruise ships. These scenarios led to rapid infection and a high death toll of the individuals exposed to that situation. It also presented an unconscionable dilemma to the rest of society, due to the risk for the community by allowing these individuals to be in contact with everyone else. Here, we also see how devastating the infections can be, and how prolonged isolation to curb the rate of infection can also have significant negative consequences. Therefore, there is a clear need to innovate in order to enable rapid treatment while in isolation. Taking patients out of that high risk environment is not considered safe, neither is bringing them into another high risk environment, such as a hospital.

BRIEF SUMMARY OF THE INVENTION

This invention pertains to personal use medical devices. The device and methods of use, focus on delivering treatment directly to the source of infection: the mucous membrane. It is handheld, portable, and also incorporates an external to the body closed-system UVC germicidal properties to insure safety for the patient and maximum germicidal efficiency.

The overarching theme for the use of this device is the need to decentralize pandemic healthcare by enabling safe and effective remote-care, in the form of a versatile and easy-to-use medical device. By focusing on this approach we can decrease the overburdening of hospitals. This would also enable maximum use of treatment in the general population while decreasing the risk to healthcare professionals. This method can empower patients to be equal partners in their own healthcare by enabling them to perform some of the steps in the treatment process themselves.

Advantages

Compared to conventional treatment delivery systems, this personal medical device is meant to be used easily by the lay person, similar to diabetes devices. Administering treatment is as simple as: open the device, insert the container, tilt head and inhale. The sides of the device are designed to isolate or "mask" the mucous membrane during this process. Afterwards the person's mask can be reapplied and the device automatically closes and is sterilized. This method, unlike other spray/aerosol based vaccines/treatments does not create additional aerosols and does not present an additional risk of infection; it can be easily used while in isolation. It allows for safe and rapid response to the risk of infection, and to its treatment. Delays in care, or restricted access to care, have been the largest hurdles to overcome during the pandemic, thus it is an important step forward.

Another major advantage of this device is that it relies on the most direct route of treatment delivery, the mucous membrane at the primary site of infection. This insures the most efficient delivery of treatments, which is essential in stopping highly contagious viruses. It also enables the use, wherever recommended, of less material (vaccine, treatment, etc) in order to induce the desired immune response. In nature the virus transmits via extremely small suspended particles, it does not require several the current vaccine fluid dosage. There are prior studies which widely support the notion that the respiratory route can increase the efficacy of the vaccines and may be used with liquid suspensions, as well as in powder form, the powder comprising of the essential molecules and active ingredients, thereby reducing the need for cold chain. Thus we can infer that the proposed style of vaccine delivery system may be more effective and open up the field to future developments as well. In effect this enables us to use a more effective method of vaccine distribution. This would facilitate wider distribution of doses, and help speed up immunity to the virus and/or recovery.

Since different treatments were, and continue to be, developed at different times, the versatility of this device is also essential. It may be used with viral therapeutics (antiviral drugs or concentrated convalescent plasma or Immunoglobulins) for instance, prior to the development of a vaccine. It can also be used for boosters of vaccines. We are now aware of the importance of early intervention in order to give the patient the best chance of a fast recovery, and avoiding hospitalization. This would be essential in helping the public while they wait for vaccine development and active immunity, while avoiding hospitals. There is the built-in ability to insure sanitization before and after use. This ability simply does not exist yet, in any product on the market. It can also be used to dispense vaccines, after they are developed. Thus, it enables the public to use interim-treatment measures, as well as long term active immunity measures. The design of the device, which is based on a decentralized healthcare model, insures that these treatments can be used while patients are quarantined. Therefore, it significantly improves pandemic response and management rates by proactively enabling patients to avoid the need for hospitalization via rapid easy-to-use treatments.

The focus on the mucous membrane has the added benefit of avoiding one of the most common side effects of vaccines: pain at the site of the injection and possible localized infection due to breaking of the skin barrier. By not breaking the skin and avoiding direct contact with the blood stream, it can be distributed safely in communities with a known high risk of other infections, such as HIV, without additional risk to medical health care professionals. Thus, it would help promote treatment use more efficiently and could be reused as needed to boost immunity, by simply shipping out a new dose and reusing the device, from the safety of your own home.

The main feature of the device is its ability to sanitize itself via timed UVC light cycles after each use, and thus be reused as needed by the patient. Since the device is self contained (closed-system), the patient never comes into direct contact with the UVC light and there is no danger from the light itself, unlike other open style UVC germicidal systems.

The design of the device contains a removable container which allows the incorporation of a variety of treatment options; it is multi-functional. As long as the treatment can be delivered via the mucous membrane, it can be administered easily via this device. It uses readily available, medical grade, inert materials for the body and components of the device. Thus, it is easy to manufacture and scale up as needed unlike devices which must be used in a hospital setting. It can also be shipped easily wherever is necessary.

This medical device also allows for "smart-integration" via a code (lazered/etched into the device) corresponding to each device which can be scanned into pandemic tracking apps. This allows patients and doctors to communicate remotely and keep track of their progress. Unlike currently available devices, it is not necessary for the patient and doctor to be in close proximity or in a hospital. Thus preventing the likelihood for hospitals to be overburdened.

The device was specifically created to not require any computer technology to operate in order to prevent any software malfunctions from impeding its usability. It does not require a computer to analyze results or utilize the device. The smart integration is minimalistic; in case internet connectivity is not available the patient can always call the doctor and touch base that way, and upload data to the app later on.

Unlike other commercially available UVC sanitization products, this device allows for controlled application and timing of the UVC cycle. A timer and fail-safe electromagnetic lock can be incorporated to insure quality control and efficiency in regards to each sterilization cycle. This device enables quality control and standardized results.

This device can be powered by a variety of means: batteries, rechargeable batteries, plug in and USB power cord. Since it only needs to be used for treatment and not on a day by day basis, the probability of it running out of power is virtually non-existent. It is also possible to use a solar powered battery system which can be recharged by simply allowing it to sit in the sunlight. Since the device creates a bright light when it is turned on, that is a clear visual indicator anyone can understand regardless of background or education level. A simple noise/vibration alarm can also be incorporated for anyone with vision impairments, thus it allows for easy customization. It can safely be used anywhere from cities to remote communities. These features are unlike any other device currently available.

Lastly, this device allows for extremely rapid antigen inactivation. Unlike other methods which rely on modifying the viral genome to inactivate it, and can be time consuming and involve the use of a separate virus for the delivery system, this method is extremely fast, and does not require extensive equipment. Thus it can be safely used to ship inactivated virus samples and to develop vaccines as quickly as possible. Being able to rapidly identify a new virus is extremely important in preventing a pandemic. Having access to inactivated virus quickly can speed up vaccine development significantly.

COVID-19 is the latest highly infectious respiratory virus to emerge in recent years. It is clear that it is necessary to rethink our approach to pandemic healthcare in order to avoid overwhelming the healthcare system. Developing personal use medical devices which can be used as easily as an inhaler or a diabetes testing kit can significantly improve the pandemic response efforts. This device does not require extensive training for use and enables fast results and fast treatment in order to prevent serious symptoms in patients and speed up immunity in the population.

It is understood that both the above general description and the following detailed description are exemplary and explanatory only and are not restrictive of the present invention as claimed.

BRIEF DESCRIPTION OF THE DRAWINGS

FIG. 1: Medical device with removable container prior to insertion into the device Feature:

1—thread mechanism connecting the removable container and the delivery system
2—spring hinge
3—opening curve for top lid
4—opening curve for bottom lid
5—LED UVC lights around perimeter (number and placement of lights must insure entire area of device is sanitized by at least 222 nm for both chambers)
6—magnetic area top lid
7—metal ring top lid
8—magnetic area bottom lid
9—metal ring bottom lid
10—cone tip for delivery of treatment
11—UV blocking wall
12—UVC permeable wall
13—top lid
14—removable container
15—bottom lid FIG. 2: Example of UV blocking removable container with lid depicted separately from medical device Feature:

1—UV blocking technology
2—UV blocking lid which threads on
3—inner curve to facilitate liquid movement towards opening
4—thread mechanism

DETAILED DESCRIPTION OF THE INVENTION

This medical device is completely enclosed and composed of a top container chamber and a bottom dispensing chamber with inner application cylindrical tip. Both lids are secured to the rest of the device via embedded magnets and spring hinges to insure a secure fit, and the walls of the device include LED UVC lights along the perimeter to insure the inner area is fully covered by germicidal UVC light. All parts and components of the device are made from medical grade inert materials which do not react or degrade during use, such as: quartz, graphene, silicon/other polymers, metals (i.e. Titanium) or other composites and alloys, available on the market and certified for safe use under the described conditions.

The UVC lights are LED UVC lights due to their safety and energy efficiency. Wherever the device is expected to withstand extreme stress a layer of transparent graphene can be used to reduce risk of breakage for the lights. The UVC range is 222 nm-254 nm, to insure germicidal efficacy. As an additional precaution the device is designed so that the user/patient is never exposed to the UVC light, by insuring that the circuit to turn the lights on can only be completed when the lids are in the closed position. The efficacy of UVC germicidal properties on hard surfaces and for water (fluid) samples have been well documented and are already in use for functions such as UVC air and water sanitization systems. The closed system of this medical device insures that full sanitization can be achieved for each method of use, while preventing the UVC light from reaching the patient.

Figure 2:
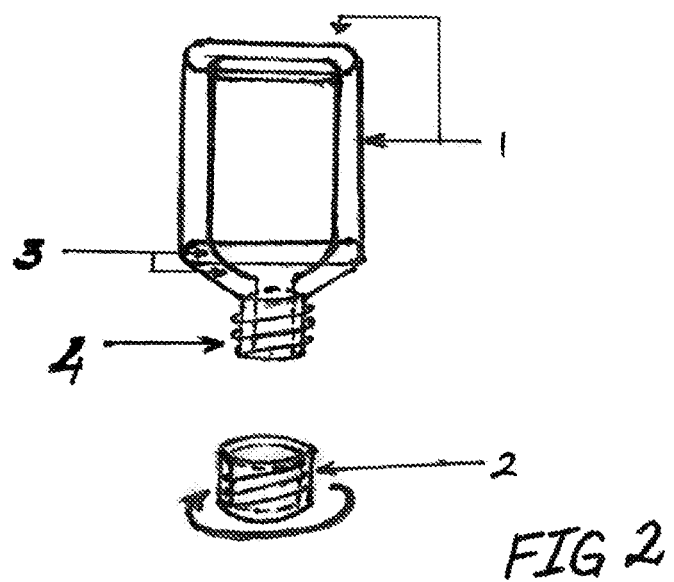

FIG. 1, shows the overall design of the device and the treatment container. FIG. 2 depicts the treatment container independently of the device with its own lid; this depicts the UV blocking technology of the removable container. For any situation where the inner product does not need to be UVC protected, a simpler model can be used, with a UVC transparent wall, instead of UVC blocking. As depicted, the device contains 2 main parts: a removable container and a delivery system which can be sterilized by disinfecting LED UVC light (FIG. 1, feature 5 and FIG. 2, feature 1). This device can deliver the medical treatments to the patients respiratory pathway.

1. Removable Container and Top Chamber

The device has a top chamber which is equipped with a removable container which is used to deliver the treatments prescribed (I.e. convalescent plasma, vaccine, other applicable respiratory pathway medical treatments, etc). The lid has a simple spring hinge and embedded magnet which secures the lid to the rest of the device body.

The removable container has several design options: The first option, is made of medical grade inert material with intrinsic UV blocking properties, or added ones, such as UV blocking film or dye (FIG. 2, feature 1)—it is isolated in order to protect the solution from any damaging environmental effects. It has a basic UV blocking (FIG. 2, feature 2) medical grade inert lid which can be easily removed as needed (twists to remove).

The second option is that this removable container is UVC permeable. This can be made from quartz, transparent graphene or other specialized UVC permeable material. This style can be useful when additional disinfection of the contents is necessary. The effects of UVC as an additional disinfection step can be used to insure hygiene of blood based products, such as plasma, without risk of damage to the necessary proteins, while safely inactivating antigens. This is a very critical quality assurance step to insure efficacy of the product.

The inside is curved in order to facilitate the liquid movement (FIG. 2, feature 3). It attaches to the rest of the device via a simple thread mechanism (FIG. 1, feature 1). The containers for the treatment are replaceable and/or disposable as needed. For example, they can be filled out by vaccine manufacturers and then sent out to patients. The shape of the container in FIG. 2, is stadium to insure easy grip and penetration of UVC light. Other shapes may also be used, such as a basic cylindrical shape.

2. Bottom Chamber for Delivery of Treatment

The bottom chamber contains a cylindrical outer shell made of medical grade inert material. The material depends on intended purposes, as described in the prior section. This encompasses the entire device, and secures the medical treatment container in place (FIG. 1). The bottom lid, similar to the top lid, also has a spring hinge and magnetic lid which allow it to snap into place, as described in the section "opening and closing details" below.

The bottom chamber delivers the treatment to the patients respiratory tract. It has UVC lights to sterilize the device along the outer circumference (FIG. 1, feature 5). The UVC light is filtered via UV blocking technology (i.e. dye, film or paint) and does not reach the user of the device.

The device-has an inner cone tip via which treatment is delivered. The cone tip (FIG. 1, feature 10) is part of the overall structure; same one piece, not an attachment. The conical tip has a simple but comfortable design with rounded edges which can deliver the medical treatment to be inhaled via the nasal airways straight into the lungs. Since the device purposefully contains no pressure system, the patient has to inhale for best use creating a negative pressure environment. An additional step is to tilt the head backwards and allow the fluid to drift down via gravity. When not in use the device can simply be stored.

The outer shell creates a barrier between the patient and the environment when the device is fitted over the patients face limiting airflow and shielding the patient. After use, the device snaps shut and is sterilized and the patient can put their mask back on if they are not in isolation.

The outer shell enclosed all parts of the device which come into contact with the patient. The purpose of the chamber is to sanitize the device automatically after each use in order to insure the sterilization of the device and prevent spread of the virus.

Opening and Closing Details

The cylindrical outer shell has a slanted and curved opening design for the top and bottom lids so as to enable ease of use (FIG. 1, feature 3,4). This allows the treatment container to be easily accessed at the top of the device. It also allows the bottom of the device, which contains the tip, to naturally fit the curved shape of the face. The lids are a complimentary fit for this shape and connected via a spring hinge (FIG. 1, feature 2). Each lid also includes a metal ring (FIG. 1, feature 7,9) imbedded in the walls and a complimentary magnetic strip (FIG. 1, feature 6,8) to connect the lid to the rest on the device. The lid can easily be snapped shut and clicks into place. The user has to hold the lid open or it springs shut.

UVC Lights Operation Details

The germicidal LED UVC lights (i.e. 222 nm-254 nm) are built into the side walls of the device to insure every part of the device which comes into contact with the patient can be sanitized. LEDs were chosen specifically due to their efficiency. The wall behind the lights is UV blocking (FIG. 1, feature 11) and the wall in front of the lights allows UVC light to pass through (FIG. 1, feature 12). In the case of a metal body for the device, the frontal wall is made out of a different, UVC permeable medical grade material.

Once the lid is closed the UVC lights turn on and remain on for a set time period. The UVC lights are guided via a contact closure timed light switch mechanism, linked to an electromagnetic fail-safe lock. The circuit is timed to insure a complete UVC cycle is run each time. Once it is completed the electrical current stops and the device reopens. This is required to ensure that the necessary time frame for UVC disinfection is fulfilled, and the device takes full advantage of the germicidal properties of UVC light. The UVC LED lights are selected for the appropriate germicidal wavelength, of at least 222 nm, up to 254 nm, since these wavelengths were shown to have effective germicidal properties. "Germicidal wavelength" is generally understood to refer to the wavelength which reaches the infectious microorganism and incapacitates it. The mechanism turns "on" when the both lids are closed, and "off" when open. The entire perimeter of the device is protected with UV blocking technology. (The sanitizer method may also be used by simply sanitizing the device via liquid sanitizer, as a fail safe.) The device can be powered by batteries or plug in. The batteries can be regular or rechargeable. The device can also be powered by rechargeable solar batteries directly or plugged into a separate solar charger.

Overall Fit—Top and Bottom Chambers

When both top and bottom parts of the device are fitted together they sit flush to each other. This is done via a thread mechanism (FIG. 1, feature 1). The top threads into the bottom. The threads are at the opening of the top container and right before it connects with the tip on the bottom container.

The device is portable, handheld, and can be given directly to patients and taken home with them; it can be used while the patient is in isolation/quarantine. It can be easily shipped and distributed in viral hotspots. It is ideally suited to integrate the use of multiple viral treatment options.

"Smart" Integration Options
1. Users can manually track results and simply upload to contact tracing apps.
2. Each device can be equipped with a scan code. Users can then scan their device and upload the data to a encrypted cloud based system, thus protecting user privacy while enabling contact tracing and rapid response. The individual can then request further assistance or treatment as needed.

Manufacturing

The device can be manufactured easily via standard techniques by any company with access to the materials needed. The main body of the device lends itself well to 3D printing techniques. The simple circuit and locking mechanism can either be made in house or purchased. The LED UVC lights can either be made or purchased from eligible manufacturers.

Material Examples:

UVC transparent: quartz, transparent graphene, or other materials, composites, alloys or polymers with these properties.

UVC blocking: glass, plastic, acrylic, silicon, Titanium, or other medical grade composites, alloys or polymers with these properties, or UVC blocking film or dye in combination with UVC permeable medical grade materials.

In most cases, simple medical grade polymers would suffice for the body of the device, with the components which need to be UVC transparent being made from materials like quartz, or any other UVC transparent material.

In cases where the target demographic is first responders, law enforcement or military personnel and the device must maintain functionality under extreme conditions, inert medical grade metals, such as medical grade Titanium, alloys, or graphene may also be used. Graphene can be used as both a metal and a thin layer of transparent graphene which is UVC permeable. Thus it is appropriate for the body of the device as well as the LED UVC lights and the UVC permeable inner container. Graphene coatings are known to increase the strength of steel, thus it can be used to increase the impact resistance of UVC permeable materials like quartz or on its own. Titanium is an excellent choice as well due to its wide availability, light weight and extremely strong structure. Unlike other metals it does not corrode in the presence of water. Both materials are an excellent choice for anyone who may need to use it under extreme conditions, although this is not intended to be a exhaustive list and other options do exist and may be used. The material variations of the device does not significantly alter its manufacturing or use.

Uses of the Medical Device

For dispensing treatments, the medical clinic or manufacturing company can simply fill the treatment container(s) and send them back to the patient. It has been well documented in the art that early administration of treatments can lead to the best results for the patient, and help avoid hospitalization. Thus, timing is of paramount importance. This device allows a safe, decentralized approach to this type of therapy which can help patients prior to hospitalization with severe symptoms, who do not have access to vaccine. The disposable container can be inserted into the device and the treatment is able to be used as liquid drops, as prescribed. The UVC light function insures sanitization and safety during use. The same principles apply for administration of any applicable drug treatments. This can also be used for boosters of vaccines to maintain strong immunity or to address variants.

For the 1st method of use, the removable container of the device would be filled with prescribed treatment. And then it would be shipped to a treatment site, such as the patients home. After receiving this container the patient would connect it to the medical device with the inner cone tip pointed upwards. It can be simply screwed on. And then the patient would enable the LED UVC lights to perform the internal sterilization cycle (this should be done after each use of the device where it comes in contact with a potential source of contamination). The device can then simply be flipped so that the prescribed fluid treatment in the removable container moves into the inner cone tip, located in the bottom chamber of the device. The lid of the bottom chamber can then be opened and the tip can be fitted to the patient to create a shield between the patient and the environment. By tilting the head, the patient can then allow the prescribed fluid treatment to come into contact with the mucous membrane of the patient and be absorbed into the body. After completing this dosage administration, the patient can close the bottom lid of the device to enable the sanitization cycle again. With this type of use, the "prescribed treatment" can comprise a vaccine, immunoglobulins, convalescent plasma, monoclonal antibodies, antiviral drugs or any approved medical treatment which can be administered via the mucous membrane.

An additional simple use for this medical device would be sample collection. The removable container can be used by the patient to collect the samples required. The container can then be recapped and sanitized. It can subsequently be used with testing reagents/strips at home, or shipped to the lab. Techniques which may still require lab processing can still be used, but the samples can be sent directly to the lab by the patients themselves, thus avoiding lineups at testing sites. For rapid tests which can be done at home, patients can share the results with their doctor right away and upload to COVID tracking apps. This will cut down on testing wait times and can be done repetitively as needed. Once the patient discovers that they have tested positively they can seek treatment right away.

For this 2nd method of use, the removable container would be filled with a testing solution, either at a lab or onsite depending on how the testing solution is applied. Afterwards, the patient themselves or a medical professional would apply the patient sample to said container and replace the lid. Following this, the removable container with the container lid attached would be placed into the top container chamber of the medical device and the LED UVC lights would be turned on to perform an internal sterilization cycle to sanitize device and the removable container. The container can then be handled safely to conduct testing of the patient sample within the removable container, either onsite or by shipping it to a lab off site, to obtain the diagnosis. Finally, it's then possible to dispense another removable container with prescribed medical treatment to administer to the patient, based on that diagnosis. For this 2nd method of use said testing solution is further comprised of rapid testing reagent or medium which can be evaluated on site or must be shipped to a lab offsite, for diagnosis. This is entirely dependent on the types of testing solution options available on the market.

Furthermore, it is also possible to use the removable container for future vaccine development. This could be essential in responding to new outbreaks as soon as possible. It may prove useful for first responders or military members when they are required to go into an infected area by enabling the group to immunize themselves as soon as possible, rather than wait for the infection to run its course through the entire group, as we saw in spring of 2020. This can be done by collecting viral samples in an UVC transparent container, and inactivating the virus right away via the UVC light function. In essence this opens up the possibility to develop "vaccine kits", which can be activated as needed if an outbreak happens. This can be done by adding the isolated spike protein isolates to a vaccine adjuvant (in case those isolated spike proteins are known and available), or using the UVC light to inactivate a viral sample obtained on site, and using those samples to create a vaccine faster. The ability to generate an immune response by using the fragments of the virus or inactivated virus has been well established in the art. This method or virus inactivation is extremely fast compared to other methods and does not require extensive lab equipment or use of other viral vectors, or cold chain. Instead it opens up the possibility to use a variety of vaccine formulations (including powders) and create fast, easy to use vaccine kits. This provides an additional method of using the body's own defence system to generate that response with minimal intervention. Confirmation that the virus has been inactivated can be obtained and shared immediately since UVC light works within minutes. This can then be added to a vaccine adjuvant which is already part of the vaccine kit. Testing can be used afterwards, to check the antigen level and again for the antibody response. These steps can all be accomplished safely while quarantine protocol is being observed. In the aforementioned examples, such as the cruise ships, the military marine ships, or any similar situation, it can make a considerable impact and save lives, by enabling those infected are able to get results right away and respond with a fast treatment. Thus they can induce immunity to the virus in at-risk personnel right away; as opposed to waiting to waiting weeks or months for new vaccine developments or simply waiting for the infection to run its course through the entire isolated population. This provides a quick alternative and fills the gap in patient care. It provides an active way of fighting the virus while in isolation without the need to wait or really on equipment which is simply out of reach.

For this 3rd method of use, the removable container can be shipped or handed out to a patient as part of a vaccine/inoculation kit. The container lid of the removable container can be taken off and a sample of viral antigen can be added to it, and then it can be recapped. After this the patient or a medical professional can enable the LED UVC lights to perform an internal sterilization cycle to insure disinfection of the device and said removable container. The removable container can then be filled with vaccine adjuvant solution from the vaccine/inoculation kit. The removable container containing the inactivated viral antigen plus adjuvant can now be attached to the medical device, similarly to method 1 above. The inner cone tip can be inserted into the nasal passage way of the patient and positioned to create a shield between the patient and the environment. Afterwards, the head of the patient can be tilted backwards to allow the inactivated viral antigen plus adjuvant in the removable container to come into contact with the mucous membrane of the patient and facilitate the inhaling process to induce an antibody response. It is then possible to remove the tip and close the bottom lid of the device to enable an internal sterilization cycle. This is again consistent with the prior methods of using the device. Finally to insure that the antibody response was achieved, antibody testing can be done to confirm the presence of the antibody response. In this instance the UVC light cycle is applied at the appropriate wavelength and timing to insure the entire device as well as the contents of the removable container are sterilized, to deactivate the viral antigen in the sample. For this 3rd method of use the removable container and lid are made from medical grade, inert, UVC transparent material only (unlike the prior uses which could have either blocking or transparent materials) to allow proper penetration of UVC light. The viral antigen may either be collected on site or it can be included in the vaccine kit, depending on the situation. As a fail-safe, in the event of a power source failure, the UVC sterilization can be done via an external or independent UVC light source of the same germicidal intensity.

Summary

Other treatment delivery systems currently available simply do not have the ability to enable a fast response to the pandemic. This is evidenced by the bottlenecks in supplies, testing/treatment lineups, and overcrowding of hospitals. They are required to be used in hospital setting and/or by a health care professional. This makes it difficult for patients to access care right away and increase the likelihood of serious illness. The high transmission rate of highly contagious viruses and need to quarantine makes it extremely risky for individuals to access in-person medical care. In addition the need for doctors to be physically present to administer every step of the treatment creates bottle necks in medical care, overwhelms hospitals and causes delays in other critical care areas. Syringes pose the risk of infection and pain and must be administered by a medical professional. Spray and aerosol delivery systems cannot be used without the risk of spreading the infection. They also cannot be sterilized effectively after use and must be disposed of immediately. None of these methods enable fast response in a viral pandemic and easy tracking of results. They all present a clear risk to healthcare professionals, as well as patients/public.

By comparison, this personal use device enables remote care and pandemic infection tracking, is versatile in terms of which treatments it can dispense, and can be easily sterilized after each use. It is easily manufactured from a variety of materials and portable. It allows patient to have confidence that the treatment they receive is safe to use due to the extra sanitization and can be easily applied. In addition it provides the ability to increase testing efficiency via rapid testing methods and direct shipment of sanitized samples. Finally, it enables the development of emergency vaccine kits, which can be used right away to induce an immune response and thus prevent infection which can be especially useful for military personnel, first responders or anyone who cannot access a hospital right away. This last function is especially useful for combating new virus variants or new viruses. It was designed as an easy to use, multi-functional, self-sterilizing device, in order to enable rapid response to infections. The UVC light is used in a closed system, thus insuring the safety of the user and reliable standardized results. It does not require specialized training to use and enables shipping of treatments to patients directly, thus resolving the overcrowding of hospitals and medical centres.

The invention claimed is:

1. A medical device, comprising:
a cylindrical frame having inner and outer walls and having a top container chamber and a bottom dispensing chamber that are internally connected; the top container chamber equipped with a removable container, a thread mechanism to connect said removable container to the top container chamber, and a top lid adapted to seal the top container chamber; the bottom chamber having an inner cone tip adapted to deliver a prescribed treatment to the nasal airways and a bottom lid adapted to seal the bottom dispensing chamber; said removable container is in fluid communication with said inner cone tip;
LED UVC lights embedded within the walls of said cylindrical frame and configured to emit radiation into the top container chamber and the bottom dispensing chamber at a germicidal wavelength at a minimum of 222 nm;
UVC blocking technology along the wall of the cylindrical frame configured to prevent exposure of UVC light radiation to any person;
a timer plus electromagnetic fail-safe locking mechanism adapted to ensure quality control and efficiency during internal sterilization cycles of the medical device;
a contact closure light switch embedded into each of the top lid and bottom lid and connected to the timer plus electromagnetic fail-safe locking mechanism to lock close the top lid and bottom lid during internal UVC disinfection and unlock the top lid and bottom lid when internal UVC sterilization is complete;
an energy power source input permanently connected to the medical device; and
a tracking code attached to said cylindrical frame.

2. A medical device as in claim 1, wherein said cylindrical frame is made from medical grade inert material, which does not degrade in response to environmental factors or due to UVC light.

3. A medical device as in claim 1, wherein said top lid and said bottom lid are attached to said medical device via a spring loaded hinge.

4. A medical device as in claim 1, wherein said top lid and said bottom lid have an embedded magnetic strip that connects to a metal ring to connect each lid to the cylindrical frame.

5. A medical device as in claim 1, wherein said removable container comprises a container lid which is manufactured from medical grade inert material which does not degrade in response to environmental factors or due to UVC light.

6. A medical device as in claim 1, wherein said removable container may be UVC blocking or UVC transparent as needed, depending on intended use.

7. A medical device as in claim 1, wherein the energy power source input comprises of any type of battery or batteries, a USB cable charger, or a solar energy charger.

8. A method of using the medical device of claim 1 comprising the steps of:
filling a removable container with a prescribed fluid treatment;
shipping said removable container to a treatment site;
connecting said removable container to the medical device with the inner cone tip pointed upwards;
enabling the LED UVC lights to perform internal sterilization cycles after each use;
flipping the removable container so the prescribed fluid treatment moves into the inner cone tip;
opening the lid with the tip and fitting the opening to the patient to create a shield between the patient and the environment;
tilting the head of the patient to allow the prescribed fluid treatment to come into contact with the mucous membrane of the patient and be absorbed into the body of the patient;
closing the bottom lid of the device to enable the sterilization cycle after use.

9. The method of claim 8, wherein said prescribed treatment further comprises vaccine, immunoglobulins, convalescent plasma, monoclonal antibodies, antiviral drugs or any approved medical treatment which can be administered via the mucous membrane.

10. The method of claim 8, wherein said sterilization cycle may be performed via an external or independent UVC light source or a sanitizer solution in the event of a power source failure within the device.

11. A method of using the medical device of claim 1, comprising the steps of:
filling the removable container with a testing solution;
applying the patient sample to said container and replacing lid;
placing the removable container with the container lid attached to the removable container into the top container chamber;
enabling the LED UVC lights to perform an internal sterilization cycle to sanitize device;
conducting testing of the patient sample within the removable container, either on site or by shipping it to a lab off site, to obtain diagnosis;
and dispensing another removable container with prescribed medical treatment to administer to a patient.

12. The method of claim 11, wherein said testing solution is further comprised of rapid testing reagent or medium which can be evaluated on site, or must be shipped to a lab offsite, for diagnosis.

13. A method of using the medical device of claim 1, comprising the steps of:
shipping or giving the removable container to a patient as part of a vaccine/inoculation kit;
removing the container lid of said removable container;
applying a sample antigen to be inactivated or which is already inactive to said removable container;
reconnecting the container lid to said removable container;
enabling the LED UVC lights to perform an internal sterilization cycle to insure disinfection of the device and said removable container;
filling the removable container with a vaccine adjuvant solution from the vaccine/inoculation kit;
connecting the removable container containing the inactivated viral antigen plus the vaccine adjuvant solution to the medical device;
fitting the inner cone tip into the nasal passage way of the patient to create a shield between the patient and the environment;
tiling the head of the patient using the medical device backwards to allow the inactivated viral antigen plus the vaccine adjuvant solution in the removable container to come into contact with the mucous membrane of the patient and facilitate the inhaling process to induce an antibody response;
closing the bottom lid of the device to enable an internal sterilization cycle after use; and,
performing antibody testing to insure adequate antibody response.

14. The method of claim 13, wherein said active or inactive antigen is further comprised of either a viral sample collected on site, or a viral protein isolate obtained offsite and shipped to the patient; the active antigen would become inactivated after treatment with the sterilizing UVC light, prior to shipping.

15. The method of claim 14, wherein said removable container is further comprised of inert medical grade UVC transparent material.

16. The method of claim 13, wherein said UVC light cycle is applied at the appropriate intensity and time interval to insure sanitization or germicidal effect of the removable container contents, as well as the entire chambers of the device.

17. A medical device as in claim 1, wherein said emission of radiation at a germicidal wavelength and internal UVC disinfection may be done via external or independent sanitization methods in the event of a power source failure within the device.

* * * * *